(12) United States Patent
Huchel et al.

(10) Patent No.: US 8,680,040 B2
(45) Date of Patent: Mar. 25, 2014

(54) 1-AZA-3,7-DIOXABICYCLO[3,3,0]OCTANE COMPOUNDS AND MONOCYCLIC OXAZOLIDINES AS PRO-FRAGRANCES

(75) Inventors: Ursula Huchel, Cologne (DE); Thomas Gerke, Neuss (DE); Silvia Sauf, Duesseldorf (DE); Claudia Klink, Willich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 479 days.

(21) Appl. No.: 12/486,348

(22) Filed: Jun. 17, 2009

(65) Prior Publication Data

US 2009/0312231 A1 Dec. 17, 2009

Related U.S. Application Data

(63) Continuation of application No. PCT/EP2007/062875, filed on Nov. 27, 2007.

(30) Foreign Application Priority Data

Dec. 20, 2006 (DE) .......................... 10 2006 060 943

(51) Int. Cl.
*A61K 8/00* (2006.01)
*A61K 8/18* (2006.01)
*A61Q 13/00* (2006.01)
*C11D 3/50* (2006.01)
*C11D 9/44* (2006.01)
*C11D 3/37* (2006.01)
*C07F 7/02* (2006.01)
*C07F 7/10* (2006.01)
*C07F 7/04* (2006.01)
*C07F 7/00* (2006.01)
*A61K 8/02* (2006.01)

(52) U.S. Cl.
USPC ............... 512/10; 510/101; 510/466; 512/25; 512/27; 556/400; 556/413; 556/457; 556/458; 424/401

(58) Field of Classification Search
USPC ......... 510/101, 466; 512/10, 25, 27; 524/487; 528/15, 24, 31; 424/401; 556/457, 458, 556/400, 413
See application file for complete search history.

(56) References Cited

U.S. PATENT DOCUMENTS

| | | | |
|---|---|---|---|
| 3,215,719 A | 11/1965 | Allen et al. | |
| 3,824,309 A * | 7/1974 | Schnegelberger | 514/374 |
| 6,090,399 A * | 7/2000 | Ghosh et al. | 424/409 |
| 6,861,402 B1 | 3/2005 | Miracle et al. | |
| 2002/0155985 A1* | 10/2002 | Miracle et al. | 512/10 |
| 2003/0207786 A1 | 11/2003 | Miracle et al. | |
| 2004/0029750 A1* | 2/2004 | Schudel et al. | 510/101 |
| 2004/0067870 A1 | 4/2004 | Miracle | |
| 2004/0072704 A1* | 4/2004 | Gerke et al. | 510/101 |
| 2006/0236470 A1 | 10/2006 | Sabnis et al. | |

FOREIGN PATENT DOCUMENTS

| | | | | |
|---|---|---|---|---|
| CA | 1110806 | 10/1981 | | |
| DE | 28 44 789 C2 | 6/1986 | | |
| EP | 0 414 962 B1 | 3/1994 | | |
| JP | H03-190815 | * 12/1989 | ............... | A61K 7/50 |
| JP | 2004-143638 | * 5/2004 | ............... | C11B 9/00 |
| WO | WO 99/07764 | 2/1999 | | |
| WO | WO 99/09083 | 2/1999 | | |

OTHER PUBLICATIONS

Pierce et al. (J. Am. Chem. Soc. pp. 2595-2596, Jun. 1951).*
Senkus ( J. Am. Chem. Soc. pp. 1515-1519 vol. 67, 1945).*
Heidrun Steimann et al., "Umalkoxylierung in der siliciumorganischen Chemie," *Z. Chem.*, No. 3, 1977, pp. 89-92.
International Search Report of PCT/EP2007/062875, dated Feb. 13, 2008.

* cited by examiner

*Primary Examiner* — Patrick Ryan
*Assistant Examiner* — Aaron Greso
(74) *Attorney, Agent, or Firm* — RatnerPrestia

(57) ABSTRACT

Silicic acid esters to which fragrances are bound, preferably as 1-aza-3,7-dioxabicyclo[3,3,0]octane compounds or as monocyclic oxazolidines and that are suitable for adding fragrance to detergents and cleaning agents because they release the bound fragrances in hydrolysis.

10 Claims, No Drawings

1 - A Z A - 3 , 7 - D I O X A B I C Y C L O [ 3 , 3 , 0 ] O C T A N E COMPOUNDS AND MONOCYCLIC OXAZOLIDINES AS PRO-FRAGRANCES

CROSS-REFERENCE TO RELATED APPLICATIONS

This application is a continuation under 35 U.S.C. §§120 and 365(c) of International Application PCT/EP2007/062875, filed on Nov. 27, 2007. This application also claims priority under 35 U.S.C. §119 of DE 10 2006 060 943.3, filed on Dec. 20, 2006. The disclosures of PCT/EP2007/062875 and DE 10 2006 060 943.3 are incorporated herein by reference in their entirety.

BACKGROUND OF THE INVENTION

The invention relates to silicic acid esters to which fragrances are bound, preferably as 1-aza-3,7-dioxabicyclo[3,3,0]octane compounds or as monocyclic oxazolidines, and are suitable for adding fragrance to detergents and cleaning agents because they release the bound fragrances in hydrolysis.

Controlled release of ingredients in a wide variety of preparations, known as "controlled release," is the subject matter of numerous publications and patent applications. In the field of detergents and cleaning agents, accelerated or delayed release of ingredients from the group of bleaching agents, bleach activators, surfactants, etc. is of special interest. Of excellent importance in this field is the release of fragrances because the product as well as the detergent and cleaning solution and the items treated with these agents are to be perfumed intensely and with a long-lasting effect. The situation is similar for cosmetic agents, but instead of the perfuming of a product there, rather it is the perfuming of skin or hair that is to be accomplished.

A fundamental problem in the use of fragrances here is that these are naturally volatile substances; otherwise no fragrance effect could be achieved. Therefore, with regard to the use of fragrances in detergents and cleaning agents, one is confronted with the same problem as in the use of cosmetic preparations, that although the fragrances are naturally volatile compounds, on the other hand one would like to achieve a long-lasting fragrance effect that is as uniform as possible. In addition, the fragrance impression of a perfume changes over time because the scents representing the fresh and light notes in the perfume evaporate more rapidly due to their high vapor pressure than the fragrances representing the heart notes and base notes.

In addition to the methods of applying fragrances to carrier materials and coating the scented carriers, or encapsulating fragrances or incorporating them into compounds (e.g. cyclodextrin-perfume complexes), there is also the possibility of chemically binding the fragrances to carrier media, whereby the chemical bond is broken and the fragrance is released slowly. Such a carrier-bound precursor of a fragrance is also known as a "pro-fragrance," "pro-accord" or "fragrance delivery substance." Examples of converting a fragrance into a carrier-bound precursor include the esterification of fragrance alcohols, and there is an extensive state of the art for this group of substances.

In the state of the art, there have been several proposals for binding fragrance alcohols to nonvolatile siloxanes from which they are released slowly by hydrolysis. Although there is also an extensive state of the art in siloxane esters of fragrance alcohols, problems often occur when using the aforementioned compounds in detergents and cleaning agents. Thus many of the known compounds cannot always be used in aqueous detergents and cleaning agents because they undergo hydrolysis even in the product and the delayed release therefore no longer occurs at a later point in time. This is even more so because the usual detergents and cleaning agents often have pH levels which further promote hydrolysis. Incorporation of the known siloxane esters into powdered detergents and cleaning agents is no longer so simple. Under conventional production conditions for compressed particle mixtures such as granulation or press agglomeration, the siloxane esters also tend to release the fragrance alcohol already during production, i.e. too early. There is therefore a need for providing fragrance precursors which will perfume the product, e.g. detergents and cleaning agents, as well as substrates treated with the products, in particular textiles, having the longest lasting effect possible.

Monomeric orthosilicic acid esters of fragrance alcohols are described in U.S. Pat. No. 3,215,719 (Dan River Mills), for example. This document also mentions delayed release of perfuming alcohols from mixed esters such as bis(eugenyloxy)-diethoxysilane or bis(cinnamoyloxy)diethoxysilane, whereby the central Si need not necessarily be bound only to oxygen. Oligomeric siloxane esters are not described in that publication.

Powdered or granular detergents and cleaning agent compositions containing silicon compounds "imparting a pleasant odor" are described in DE 28 44 789 (Dow Corning). The monomeric, oligomeric and polymeric silicon compounds disclosed therein do not necessarily have a central Si atom surrounded by four oxygen atoms. Oligomeric Si compounds with more than one fragrance alcohol ester group are also not described in this publication. US 20030207786 and US 20040067870 also describe pro-fragrances having an oxazolidine structure.

U.S. Pat. No. 6,861,402 describes pro-fragrances containing a fragrance aldehyde or a fragrance ketone in the form of an oxazolidine. For example, N-benzene-ethanolamine is reacted with a fragrance to yield a monocyclic oxazolidine.

DESCRIPTION OF THE INVENTION

The object of the present invention was therefore to provide fragrance precursors, so-called "pro-fragrances," in particular for aldehyde fragrances and ketone fragrances. The object was in particular to provide hydrolysis-stable siloxane esters of fragrances which can be incorporated into aqueous detergents and cleaning agents without already being subject to excessive hydrolysis phenomena in the product. The incorporability of the compounds into granular detergent and cleaning agent compositions without resulting in decomposition during the production process is also a requirement of the compounds to be provided. In addition, the substrates treated with the inventive compounds should have a pleasant and long-lasting fragrance.

It has now surprisingly been found that fragrances bound as 1-aza-3,7-dioxabicyclo[3,3,0]octane compounds (bicyclic oxazolidine derivatives) and/or as monocyclic oxazolidines to silicic acid esters easily yield very suitable pro-fragrances for use in detergents and cleaning agents as well as cosmetic preparations. In addition, it has been found according to the invention that cyclic and/or monocyclic oxazolidine derivatives of fragrance aldehydes and fragrance ketones in particular allow a reduction in the vapor pressure of the fragrance aldehydes and fragrance ketones and make the fragrance impression longer-lasting. Furthermore, deposition of the aforementioned compounds on solid surfaces such as textiles, skin or hard surfaces can thereby be improved. It has been discovered here that the silicic acid esters are preferably in the form of a mixture of esters of other oligosilicic acids.

Of the surprising properties, it should be emphasized that these compounds are largely resistant to hydrolysis in detergents and cleaning agents and in cosmetics, but a delayed-release effect can be achieved in the desired manner in use of the detergents and cleaning agents as well as cosmetics (cosmetic agents) containing the inventive pro-fragrances. In particular a long-lasting fragrance effect on the treated laundry can be achieved, e.g. with a fabric rinse containing pro-fragrance according to the invention; this may be attributed to the fact that the inventive pro-fragrances adhere to the laundry and the fragrances (fragrance aldehydes and/or fragrance ketones) are released by hydrolysis after exposure to atmospheric humidity.

The subject matter of the present invention is therefore silicic acid esters bound to fragrances and/or perfumes, which are preferably released by hydrolysis over a longer period of time and thus produce a long-lasting fragrance perception. The fragrances and/or perfumes are preferably present in the form of bicyclic and/or monocyclic oxazolidine derivatives.

The subject matter of the present invention is thus silicic acid esters of the general formula (I)

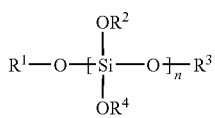

(I)

where at least one of the residues $R^1$, $R^2$, $R^3$ and $R^4$ independently of one another denotes (a) a 1-aza-3,7-dioxabicyclo[3,3,0]octane compound of general formula (II),

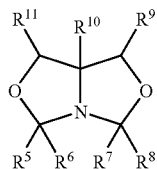

(II)

where $R^5$, $R^6$, $R^7$, $R^8$ independently of one another denote hydrogen, an alkyl residue with 1 to 8 carbon atoms or residues, which in a compound of the general formula $R^5$—C(=O)—$R^6$ and/or $R^7$—C(=O)—$R^8$ yield a fragrance, in particular a fragrance aldehyde or a fragrance ketone, where $R^5$ and $R^6$ and/or $R^7$ and $R^8$ cannot be hydrogen at the same time, $R^9$, $R^{11}$ independently of one another denote hydrogen, an alkyl residue with 1 to 8 carbon atoms, hydroxyalkyl with 1 to 8 carbon atoms, aminoalkyl, $R^{10}$ is a bond or a divalent alkylene residue with 1 to 8 carbon atoms, and/or (b) a monocyclic oxazolidine of general formula (III),

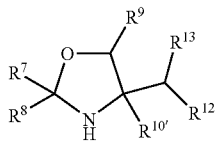

(III)

with the meanings given above for the residues $R^7$, $R^8$, $R^9$ and $R^{10'}$ denotes a bond or a divalent alkylene residue with 1 to 8 carbon atoms, hydrogen, an alkyl residue which may be substituted by one or two hydroxyl groups and/or an amino group and/or in which up to 8 nonvicinal —$CH_2$ groups may be replaced by —O—, and $R^{12}$ denotes hydrogen, an alkyl residue with 1 to 8 carbon atoms, hydroxyalkyl with 1 to 8 carbon atoms or aminoalkyl, $R^{13}$ is an OH group or a bond, and the remaining residues $R^1$, $R^2$, $R^3$ and $R^4$ independently of one another are selected from hydrogen, an alkyl residue with 1 to 20 carbon atoms or fragrance alcohol residue, and n assumes values from the range of 2 to 20.

In the compounds of general formula (I), in which the residues $R^1$, $R^2$, $R^3$ and/or $R^4$ independently of one another may denote compounds of formulas (II) and/or (III), $R^5$, $R^6$, $R^7$ and $R^8$ independently of one another denote residues which preferably yield a fragrance aldehyde or a fragrance ketone in a compound of the general formula $R^5$—C(=O)—$R^6$ and/or $R^7$—C(=O)—$R^8$. $R^5$ and $R^6$ and/or $R^7$ and $R^8$ in formula (II) may not be hydrogen at the same time. The residues $R^5$ and $R^6$ in the structural element —$CR^5R^6$ and the residues $R^7$ and $R^8$ in the structural element —$CR^7R^8$ preferably have at least six carbon atoms together, preferably at least five carbon atoms. In the compounds of general formula (I), the fragrance aldehydes and/or fragrance ketones are thus preferably present in derivatized form as a 1-aza-3,7-dioxabicyclo[3,3,0]octane compound (bicyclic oxazolidine) of general formula (II) and/or as a monocyclic oxazolidine of general formula (III). All the usual fragrance aldehydes and fragrance ketones that are typically used to achieve a pleasant fragrance perception may be used as the fragrance aldehydes or fragrance ketones here. Fragrances and perfumes are to be understood as being synonymous within the scope of the present invention.

According to the present invention, "fragrance ketones" are fragrances having at least one free ketone group. Mixtures of different ketones may also be used. Fragrance ketones are preferably selected from the group comprising buccoxime, isojasmone, methyl beta-naphthyl ketone, musk indanone, tonalide/musk plus, alpha-damascone, beta-damascone, delta-damascone, isodamascone, damascenone, damarose, methyl dihydrojasmonate, menthone, carvone, camphor, fenchone, alpha-ionene, beta-ionone, dihydro-beta-ionone, fleuramone, dihydrojasmone, cis-jasmone, Iso E Super, methyl cedrenyl ketone or methyl-cedrylone, acetophenone, methylacetophenone, para-methoxy-acetophenone, methyl beta-naphthyl ketone, benzylacetone, benzophenone, para-hydroxyphenyl-butanone, celery ketone or livescone, 6-isopropyldecahydro-2-naphthone, dimethyl octenone, Frescomenthe, 4-(I-ethoxyvinyl)-3,3,5,5,-tetra-methyl-cyclohexanone, methyl heptenone, 2-(2-(4-methyl-3-cyclohexen-1-yl)-propyl)cyclopentanone, 1-(p-menthen-6(2)-yl)-1-propanone, 4-(4-hydroxy-3-methoxyphenyl)-2-butanone, 2-acetyl-3,3-dimethyl-norbornane, 6,7-dihydro-1,1,2,3,3-pentamethyl-4(5H)-indanone, 4-damascol, dulcinyl or cassione, gelsone, hexylone, isocyclemone E, methyl cyclocitrone, methyl lavendel ketone, orivone, para-tert-butylcyclohexanone, verdone, delphone, muscone, neobutenone, plicatone, veloutone, 2,4,4,7-tetramethyl-oct-6-en-3-one, tetrameran, hedion and mixtures thereof. The ketones may preferably be selected from alpha-damascone, delta-damascone, isodamascone, carvone, gamma-methylionone, Iso E Super, 2,4,4,7-tetramethyl-oct-6-en-3-one, benzylacetone, beta-damascone, damascenone, methyl dihydrojasmonate, methyl cedrylone, hedione and mixtures thereof.

According to the invention, "fragrance aldehydes" are fragrances having at least one free aldehyde group. Suitable fragrance aldehydes may be any aldehydes which impart a desired fragrance or fresh perception according to the fragrance ketones. These may in turn be individual aldehydes or aldehyde mixtures. From the large group of fragrance aldehydes, the following preferred representatives can be mentioned: octanal, citral, melonal, lilial, Floralozone, canthoxal, 3-(4-ethylphenyl)-2,2-dimethylpropanal, 3-(4-methoxyphenyl)-2-methyl-propanal, 4-(4-hydroxy-4-methylpentyl)-3-cyclohexene-1-carboxaldehyde, phenylacetaldehyde, methyl nonyl acetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropyl-phenyl)-2-methylpropan-1-al, 3-(4-ethylphenyl)-2,2-dimethylpropan-1-al, 3-(4-tert-butylphenyl)-2-methyl-propanal, 3-(3,4-methylenedioxyphenyl)-2-methylpropan-1-al, 3-(4-ethylphenyl)-2,2-dimethylpropanal, 3-(3-isopropylphenyl)butan-1-al, 2,6-dimethylhept-5-en-1-al, n-decanal, n-undecanal, n-dodecanal, 3,7-dimethyl-2,6-octadien-1-al, 4-methoxybenzaldehydes, 3-methoxy-4-hydroxybenzaldehydes, 3-ethoxy-4-hydroxybenzaldehydes, 3,4-methylenedioxybenzaldehyde and 3,4-dimethoxybenzaldehyde, adoxal, anisaldehyde, cumal, ethylvanillin, florhydral, helional, heliotropin, hydroxycitronellal, koavone, lauryl aldehyde, lyral, methyl-nonylacetaldehyde, bucinal, phenylacetaldehyde, undecylenealdehyde, vanillin, 2,6,10-trimethyl-9-undecenal, 3-dodecen-1-al, alpha-n-amylcinnamaldehyde, 4-methoxybenzaldehyde, benzaldehyde, 3-(4-tert-butylphenyl)-propanal, 2-methyl-3-paramethoxyphenylpropanal, 2-methyl-4-(2,6,6-trimethyl-2(I)-cyclohexen-1-yl)butanal, 3-phenyl-2-propenal, cis-/trans-3,7-dimethyl-2,6-octadien-1-al, 3,7-dimethyl-6-octen-1-al, [(3,7-dimethyl-6-octenyl)oxy] acetaldehyde, 4-isopropylbenzaldehyde, 1,2,3,4,5,6,7,8-octahydro-8,8-dimethyl-2-naphthaldehyde, 2,4-dimethyl-3-cyclohexene-1-carboxaldehyde, 1-decanal, decylaldehyde, 2,6-dimethyl-5-heptenal, 4-(tricyclo[5.2.1.0(2,6)]-decylidene-8)-butanal, octahydro-4,7-methano-1-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cumene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethyl-cyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-meth-oxyhexahydro-4,7-methanoindane-1- or 2-carboxaldehyde, 3,7-dimethyl-octan-1-al, 1-undecanal, 10-undecen-1-al, 4-hydroxy-3-methoxybenzaldehyde, 1-methyl-3-(4-methylpentyl)-3-cyclohexene-carboxalde-hyde, 7-hydroxy-3,7-dimethyloctanal, trans-4-decenal, 2,6-nonadienal, para-tolylacetaldehyde, 4-methylphenyl-acetaldehyde, 2-methyl-4-(2,6,6-trimethyl-1-cyclohexen-1-yl)-2-butenal, ortho-methoxycinnamaldehyde, 3,5,6-trimethyl-3-cyclohexenecarboxaldehyde, 3,7-dimethyl-2-methylene-6-octenal, phenoxy-acetaldehyde, 5,9-dimethyl-4,8-decadienal, peonyaldehyde (6,10-dimethyl-3-oxa-5,9-undecadien-1-al), hexahydro-4,7-methanoindane-1-carboxaldehyde, 2-methyl-octanal, alpha-methyl-4-(1-methylethyl)benzolacetaldehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo-[2.2.1]-hept-5-ene-2-carbaldehyde, 9-decenal, 3-methyl-5-phenyl-1-pentanal and methyl nonyl acetaldehyde.

For other suitable fragrances, selected from aldehydes and ketones, reference is made to *Steffen Arctander, Aroma Chemicals* vol. 1: 0-931710-37-5, *Aroma Chemicals* vol. 2: 0-931710-38-3, published 1960 and 1969, respectively, reprinted 2000 ISBN.

Within the scope of the present invention, the term "perfume alcohol residues" is understood to refer to perfumes having free hydroxyl groups that can be esterified, regardless of the remaining structure of the molecule. Thus, salicylic acid esters can also be used as perfume alcohols. Preferred representatives can be mentioned from the large group of perfume alcohols, so that within the scope of the present invention, silicic acid esters in which $R^1$, $R^2$, $R^3$, $R^4$ independently of one another may be selected from the group of the following perfume alcohols are preferred: 10-undecen-1-ol, 2,6-dimethylheptan-2-ol, 2-methylbutanol, 2-methyl-pentanol, 2-phenoxyethanol, 2-phenyl-propanol, 2-tert-butycyclohexanol, 3,5,5-trimethylcyclohexanol, 3-hexanol, 3-methyl-5-phenylpentanol, 3-octanol, 3-phenylpropanol, 4-heptenol, 4-isopropylcyclo-hexanol, 4-tert-butycyclohexanol, 6,8-dimethyl-2-nonanol, 6-nonen-1-ol, 9-decen-1-ol, α-methyl-benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethylbenzylcarbinol, dimethylheptanol, dimethyloctanol, ethyl salicylate, ethylvanilin, eugenol, farnesol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol.

Within the scope of the present invention, "alkyl residues" are understood to be alkyls that are substituted or unsubstituted, saturated or unsaturated, branched or linear. According to the present invention, alkyls having 1 to 20 carbon atoms are preferred, 1 to 8 carbon atoms are especially preferred and 1 to 4 carbon atoms are most especially preferred. Preferred alkyl residues include, for example, methyl, ethyl, propyl, isopropyl, butyl, tert-butyl, pentyl, hexyl, heptyl, octyl, but also unsaturated alkyls, e.g. ethene, propene, butene, pentene, hexene, octene, which may be further substituted or unsubstituted. Preferred in particular are methyl, ethyl, propyl, isopropyl, octyl, butene, hexene, octene, which may be substituted or unsubstituted.

Within the scope of the present invention, "divalent alkylene residues" is understood to refer to alkyl residues which may enter into a bond at both ends, so that at one end there is a bond to the bicyclic oxazolidine (the 1-aza-3,7-dioxabicyclo[3,3,0]octane compound of general formula (II)) and on the other end the bond to the oxygen of the compound of general formula (I).

According to the invention, such an inventive silicic acid ester may have the following general structure, for example:

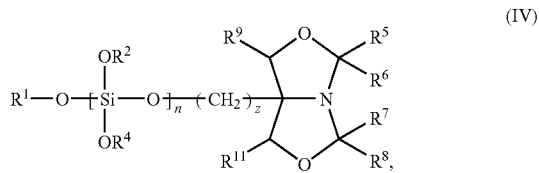
(IV)

where the residues $R^1$, $R^2$, $R^4$, $R^5$, $R^6$, $R^7$, $R^8$, $R^9$ and $R^{11}$ and n have the meanings given above, and z assumes a number from 0 to 8, preferably 1 to 4, most especially preferably 1 or 2. As shown in formula (IV), the bonding of the 1-aza-3,7-dioxa-bicyclo[3,3,0]octane compound of general formula (II) is preferably by way of the $R^{10}$ residue to the silicic acid ester of general formula (I), where $R^{10}$ is the divalent alkylene residue which may be preferably substituted or unsubstituted, saturated or unsaturated. Divalent alkylene residues with 1 to 8 carbon atoms are preferred. Preferred alkylene residues are selected from, for example: —$CH_2$-(methylene), —$CH_2$—$CH_2$— (ethylene), —$CH_2$—$CH_2$—$CH_2$— (propylene), —$CH_2$—$CH_2$—$CH_2$—$CH_2$— (butylene), —$CH_2$—$CH_2$—$CH_2$—$CH_2$—$CH_2$— (pentylene), —$CH_2$—$CH_2$—$CH_2$—$CH_2$—$CH_2$—$CH_2$— (hexylene), —$CH_2$—$CH_2$—$CH_2$—$CH_2$—$CH_2$—$CH_2$—$CH_2$— (heptylene), —$CH_2$—$CH_2$—$CH_2$—$CH_2$—$CH_2$—$CH_2$—$CH_2$—$CH_2$— (octylene), but also the branched derivatives thereof, such as isopropylene, tert-butylene; especially preferred are methylene, ethylene and propylene and/or isopropylene; methylene and ethylene are most especially preferred.

The term "bonding" within the scope of the present invention is understood to denote a single bond which forms a bond between the molecule according to general formula (II) or (III) and the compound according to general formula (I). According to the invention, another inventive silicic acid ester may thus have the following general structure, for example:

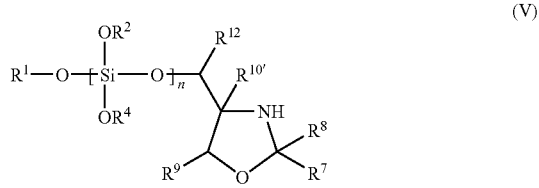
(V)

where the residues $R^1$, $R^2$, $R^4$, $R^7$, $R^8$, $R^9$, $R^{10}$ and $R^{12}$ and n have the meanings given above. As shown in formula (V), the bonding of compound (III) to (I) preferably takes place via $R^{13}$ which in this case is simply a bond.

It is also possible for the bond to be via $R^{10'}$ which then preferably a divalent alkylene residue. Such an inventive silicic acid ester is represented by the following general structure (VI), for example:

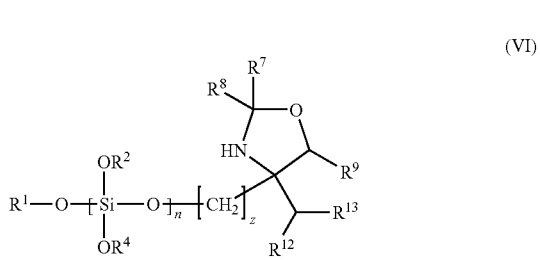
(VI)

where the residues $R^1$, $R^2$, $R^4$, $R^7$, $R^8$, $R^9$ and $R^{12}$ and n have the meanings given above and z is a number from 0 to 8, preferably 1 to 4, most especially preferably 1 or 2, and in this case $R^{13}$ is preferably an OH group.

Within the scope of the present invention, "hydroxyalkyls" are understood to be alkyl residues substituted with at least one hydroxyl group (—OH) at any site. Such a hydroxyalkyl preferably has at least one, especially two OH groups, where the preferred alkyl residues were already described above.

Within the scope of the present invention, "aminoalkyls" are understood to be alkyl residues substituted with at least one amino group (—$NH_2$) at any site. The amino group may in turn be substituted, so that it is not necessarily a terminal (primary) amine. Such an aminoalkyl preferably has at least one, especially two amino groups.

The inventive silicic acid esters are preferably used as pro-fragrances. As already explained above, pro-fragrances are carrier-bound precursors of a fragrance, where the chemical bond of the derivatized fragrance is slowly cleaved and the fragrance is released again. In a preferred embodiment, therefore at least one of the structural elements —$CR^5R^6$ or —$CR^7R^8$ of the general formula (II) in such an inventive silicic acid ester breaks up into a compound of the general formula $R^5$—C(=O)—$R^6$ or $R^7$—C(=O)—$R^8$ which has the property of a fragrance. Both structural elements —$CR^5R^6$ and —$CR^7R^8$ in formula (II) preferably break up into compounds of the general formula $R^5$—C(=O)—$R^6$ and $R^7$—C(=O)—$R^8$ which have fragrance properties.

In another preferred embodiment, $R^5$, $R^7$, $R^9$, $R^{11}$ denote hydrogen, and $R^5$ and $R^6$ in the structural element —$CR^5R^6$ and $R^7$ and $R^8$ in the structural element —$CR^7R^8$ each together have at least six carbon atoms, preferably at least five carbon atoms.

In another preferred embodiment, the structural element —$CR^7R^8$ of the general formula (III) in an inventive silicic acid ester, which has at least one monocyclic oxazolidine of the general formula (III), breaks down into a compound of the general formula $R^7$—C(=O)—$R^8$, which has the property of a fragrance.

In another preferred embodiment of the present invention, some of the perfumes are present in derivatized form as a 1-aza-3,7-dioxabicyclo[3,3,0]octane compound of general formula (II) and/or as a monocyclic oxazolidine of general formula (III) bound to the silicic acid ester of general formula (I). These are preferably perfume aldehydes and perfume ketones, which are used in such an inventive carrier-bound precursor. However, it is also possible for some of the perfumes, preferably perfume alcohols, to be esterified directly on the silicic acid ester (e.g. $R^1$=geranyl). These carrier-bound fragrance precursors may of course also be present in one molecule (formula (I)) at the same time. The different fragrances that are desired for delayed release of fragrance (aldehydes, ketones, alcohols) may thus be bound directly and/or as a 1-aza-3,7-dioxabicyclo[3,3,0]octane compound (e.g. structure IV) to silicic acid esters of general formula (I).

Likewise, fragrance aldehydes and fragrance ketones may also be bound as a compound of general formula (III) to the silicic acid esters at the same time.

In another preferred embodiment, an inventive pro-fragrance consists of the combination of structure (V) with structure (VI). In such a case, for example, the residue $R^{10'}$ (in structure (V)) is preferably a divalent alkylene residue to which a silicic acid ester is bound (like structure (VI)), which in turn may contain other fragrances in different ways, resulting in a crosslinking structure.

The inventive silicic acid esters may be used as the sole fragrance but it is also possible to use fragrance mixtures consisting only partially of the inventive pro-fragrances. Such mixtures have the advantage that the components of the fragrance mixture, which are not present in the form of silicic acid esters, are also improved with regard to the stability of the fragrance impression. In particular fragrance mixtures containing 1 to 50 wt %, preferably 5 to 40 wt % and in particular max. 30 wt % silicic acid ester may be used. In other embodiments in which the delayed fragrance effect of the carrier-bound form is to be used in particular, at least 30 wt %, preferably at least 40 wt % and in particular at least 50 wt % of the total perfume contained in an agent is advantageously introduced into the agent via the inventive pro-fragrances in the inventive use, while the remaining 70 wt %, preferably 60 wt % and in particular 50 wt % of the total perfume contained in the agent is sprayed in the usual way or is otherwise introduced into the agent. The inventive use may also advantageously be characterized in that the inventive silicic acid esters are used together with other fragrances.

By dividing the total perfume content of an agent, e.g. a detergent or cleaning agent, into a perfume, which is present in the form of the inventive silicic acid esters and perfume incorporated in the traditional way, a number of product characteristics can be implemented, which are possible only through the inventive use. For example, it is conceivable and possible to divide the total perfume content in the agents into two portions x and y, where the amount x consists of inventive silicic acid esters and the amount y consists of traditional perfume oils.

The only limit with the inventive silicic acid esters as pro-fragrances is that the fragrances introduced via the inventive silicic acid esters must originate from: the group of fragrance aldehydes or fragrance ketones (if bound to the silicic acid ester as a 1-aza-3,7-dioxabicyclo[3,3,0]octane compound or as a monocyclic oxazolidine) or perfume alcohols (if bound directly to the silicic acid esters).

The fragrances incorporated into the agents in a traditional way are not subject to any restrictions, however. Individual perfume compounds of natural or synthetic origin may thus be used as the perfume oils and/or fragrances, e.g. those of the type of esters, ethers, aldehydes, ketones, alcohols and hydrocarbons. However, mixtures of various perfumes, which jointly create a pleasing fragrance note are preferred.

Such perfume oils may also contain natural perfume mixtures such as those accessible from plant sources, e.g. pine oil, citrus oil, jasmine oil, patchouli oil, rose oil or ylang ylang oil. Also suitable are muscat sage oil, chamomile oil, clove oil, melissa oil, mint oil, cinnamon leaf oil, linden blossom oil, juniper berry oil, vetiver oil, frankincense oil, galbanum oil and labdanum oil as well as orange blossom oil, neroli oil, orange peel oil and sandalwood oil. Other traditional perfumes which may be used within the scope of the present invention include, for example, the essential oils, such as angelica root oil, anise oil, arnica blossom oil, sweet basil oil, bay oil, etc.

The inventive silicic acid esters are synthesized by simple transesterification of oligosilicic acid esters of low alcohols with 1-aza-3,7-dioxabicyclo[3,3,0]octane compounds containing hydroxyl groups and/or with monocyclic oxazolidines. During esterification, silicic acid rings are preferably formed in side reactions. Rings containing 3 and/or 4 silicon atoms are preferably formed. Accordingly, in another preferred embodiment, in addition to silicic acid esters of general formula (I), there is a mixture of silicic acid esters of formula (VII):

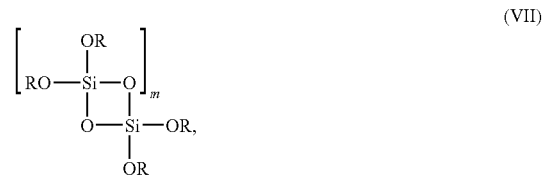

where the R residues independently of one another may assume the meanings of the residues $R^1$, $R^2$, $R^3$ and $R^4$ according to formula (I), and m is a number from 2 to 20. This aforementioned mixture preferably contains silicic acid esters of formulas (VIII) and/or (IX),

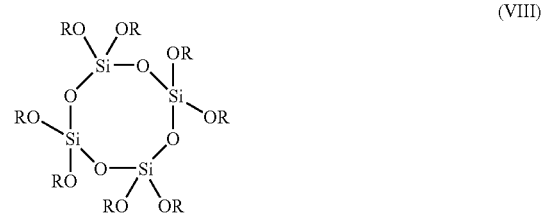

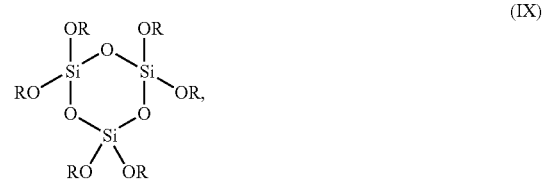

where the R residues in formulas (VIII) and (IX) independently of one another assume the meanings of the residues $R^1$, $R^2$, $R^3$ and $R^4$ according to formula (I).

Silicic acid esters of the general formula (I) therefore preferably include a mixture of different silicic acid esters which may have a cyclic structure (formulas VII, VIII, IX) as well as a linear structure (formula I) or a mixture of the two types of structures. The latter is obtained, for example, when at least one of the residues R in formulas (VII), (VIII) and (IX) in turn represents a silicic acid ester of general formula (I), where R then assumes the place of $R^1$, $R^2$, $R^3$ and/or $R^4$ in formula (I). Preferably at least half of the residues R in formula (VII), (VIII) and (IX) stand for silicic acid esters of general formula (1).

In a preferred embodiment, at least one of the residues, especially preferably at least two of the residues $R^1$, $R^2$, $R^3$, $R^4$ stands for a 1-aza-3,7-dioxabicyclo[3,3,0]octane compound of general formula (II).

This is preferably also the case for the silicic acid esters of general formulas (VII), (VIII) and (IX), that at least one of the residues R may assume the meanings of $R^1$, $R^2$, $R^3$, $R^4$ and represents a 1-aza-3,7-dioxabicyclo[3,3,0]octane compound of general formula (II). Most especially preferably, at least two, three or four of the of the residues denote a 1-aza-3,7-dioxabicyclo[3,3,0]octane compound of general formula (II). The inventive silicic acid esters preferably have as a structure the same 1-aza-3,7-dioxabicyclo[3,3,0]octane compound of general formula (II) for the residues R, $R^1$, $R^2$, $R^3$, $R^4$. However, it is also possible for the residues R, $R^1$, $R^2$, $R^3$ and $R^4$ of the inventive silicic acid esters to have different 1-aza-3,7-dioxabicyclo[3,3,0]octane compounds of general formula (II).

The bonding of 1-aza-3,7-dioxabicyclo[3,3,0]octane compound of general formula (II) is preferably by way of the residue $R^{10}$ to the silicic acid esters of general formulas (I), (VII), (VIII) and (IX). The residue $R^{10}$ is preferably a divalent alkylene residue, preferably methylene (—$CH_2$—) or ethene (—$CH_2$—$CH_2$—), especially preferably methylene (see formula IV, for example, where z=1 or 2).

The number of derivatized fragrances in a molecule determines the number of fragrances that can be released later. Accordingly, it is advantageous for a long-lasting fragrance perception if as many fragrances as possible are present in a molecule and can be released gradually by hydrolysis. It is preferable here that at least one of the structural elements —$CR^5R^6$ or —$CR^7R^8$ in an inventive silicic acid ester of general formula (I) with compounds of general formula (II) breaks down into a compound of the general formula $R^5$—C(=O)—$R^6$ or $R^7$—C(=O)—$R^8$ which has the property of a fragrance. Both structural elements —$CR^5R^6$ and —$CR^7R^8$ in formula (II) preferably break down into components of the general formulas $R^5$—C(=O)—$R^6$ and $R^7$—C(=O)—$R^8$ which have fragrance properties.

In another preferred embodiment, at least one of the residues, especially preferably at least two of the residues $R^1$, $R^2$, $R^3$, $R^4$ is a monocyclic oxazolidine of general formula (III). This is preferably also true of the silicic acid esters of general formulas (VII), (VIII) and (IX), at least one of the R residues assuming the meaning of $R^1$, $R^2$, $R^3$, $R^4$ and being a monocyclic oxazolidine of the general formula (III). Most especially preferably at least two, three or four of the residues are each a monocyclic oxazolidine of the general formula (III).

The inventive silicic acid esters here preferably have as a structure the same monocyclic oxazolidine structure of general formula (III) for the residues R, $R^1$, $R^2$, $R^3$, $R^4$ However it is also possible that the residues R, $R^1$, $R^2$, $R^3$ and $R^4$ of the inventive silicic acid esters represent different monocyclic oxazolidine structures of general formula (III).

Bonding of the monocyclic oxazolidine of general formula (III) preferably takes place here via the residue $R^{10'}$ to the silicic acid esters of general formulas (I), (VII), (VIII) and (IX). The residue $R^{10'}$ here preferably represents a divalent alkylene residue, especially methylene (—$CH_2$—) or ethene (—$CH_2$—$CH_2$—), especially preferably methylene (see, for example, formula (VI), where z=1 or 2). Bonding of the monocyclic oxazolidine of general formula (III) via the $R^{13}$ residue to the silicic acid esters of general formulas (I), (VII), (VIII) and (IX) is preferably accomplished via this residue. The $R^{13}$ residue preferably represents a bond here (see formula (V), for example). The structural element —$CR^7R^8$ in formula (III) in such cases preferably breaks down in hydrolysis and thus the fragrances are released in compounds of the general formula $R^7$—C(=O)—$R^8$.

It is of course also possible for both compounds of general formulas (II) and (III) to be present in an inventive silicic acid ester. Such an inventive pro-fragrance is also preferred because several fragrances can be released from such a molecule.

The fragrances derivatized as a 1-aza-3,7-dioxabicyclo[3,3,0]octane compounds and/or as monocyclic oxazolidines are preferably selected from the group comprising jasmones, ionones, damascones and damascenones, menthone, carvone, Iso E Super, methyl heptenone, melonal, cymal, ethylvanillin, helional, hydroxycitronellal, koavone, methyl nonyl acetaldehyde, phenyl acetaldehyde, undecylene aldehyde, 3-dodecen-I-al, alpha-n-amyl cinnamaldehyde, benzaldehyde, 3-(4-tert-butylphenyl)-propanal, 2-methyl-3-(paramethoxyphenylpropanal), 2-methyl-4-(2,6,6-trimethyl-2(1)-cyclohexen-1-yl)butanal, 3-phenyl-2-propenal, cis-/trans-3,7-dimethyl-2,6-octadien-I-al, 3,7-dimethyl-6-oct-en-I-al, [(3,7-dimethyl-6-octenyl)oxy]acetaldehyde, 4-isopropylbenzaldehyde, 2,4-dimethyl-3-cyclohexene-1-carboxyaldehyde, 2-methyl-3-(isopropylphenyl)-propanal, decylaldehyde, 2,6-dimethyl-5-heptenal, alpha-n-hexylcinnamaldehyde, 7-hydroxy-3,7-dimethyloctanal, undecenal, 2,4,6-trimethyl-3-cyclohexene-I-carboxaldehyde, 1-dodecanal, 2,4-dimethylcyclohexene-3-carboxaldehyde, 4-(4-hydroxy-4-methylpentyl)-3-cylohexene-I-carboxaldehyde, 2-methylundecanal, 2-methyldecanal, 1-nonanal, 1-octanal, 2,6,10-trimethyl-5,9-undecadienal, 2-methyl-3-(4-tertbutyl) propanal, dihydrocinnamaldehyde, 3,7-dimethyloctan-1-al, 1-undecanal, 10-undecen-1-al, 4-hydroxy-3-methoxybenzaldehyde, trans-4-decenal, 2,6-nonadienal, para-tolylacetaldehyde, 3,7-dimethyl-2-methylene-6-octenal, 2-methyl-octanal, alpha-methyl-4-(1-methylethyl)benzeneacetaldehyde, 2-methyl-3-phenyl-2-propen-1-al, 3,5,5-trimethylhexanal, 3-propyl-bicyclo[2.2.1]hept-5-ene-2-carbaldehyde, 9-decenal, 3-methyl-5-phenyl-1-pentanal, methyl nonyl acetaldehyde, citral, 1-decanal, florhydral, 2,4-dimethyl-3-cyclohexene-1-carboxaldehyde, heliotropin are especially preferred.

The inventive silicic acid esters are synthesized as explained above by simple transesterification of oligosilicic acid esters of low alcohols with hydroxyl group-containing 1-aza-3,7-dioxabicyclo[3,3,0]octane compounds and/or monocyclic oxazolidines, in which the fragrance is preferably already in derivatized form. Reaction A shows, for example, such a general synthesis with hydroxyl group-containing 1-aza-3,7-dioxabicyclo[3,3,0]octane compounds:

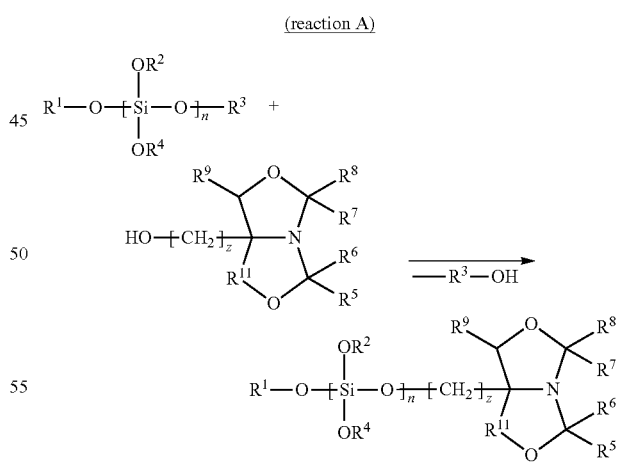

(reaction A)

where the residues $R^1$, $R^2$, $R^3$, $R^4$, $R^5$, $R^6$, $R^7$, $R^8$, $R^9$ and $R^{11}$ and n and z have the meanings given above.

The reaction of hydroxyl group-containing monocyclic oxazolidines is performed according to reaction A. Depending on the reaction time and conditions, the low alcohols are split off and the hydroxyl group containing 1-aza-3,7-dioxabicyclo[3,3,0]octane compounds or monocyclic oxazolidines are bound whereby the alcohols are more easily exchanged along Si—O—Si chains or rings than are the terminal alcohols. Such transesterifications can easily be performed as described in the publication H. Steinmann, G. Tschernko, H. Hamann, Z. *Chem.* 3, 1977, pages 89-92, for example. The contents of this publication are explicitly regarded as the disclosure content of the present patent application for the synthesis of silicic acid esters. Commercial silicic acid esters are typically used as educts. The ethanol ester, which is available from Wacker, Burghausen, may be mentioned here in particular. The transesterification can be controlled exclusively through an increase in temperature and by distilling off the low-boiling by-products. However, it is preferable if catalysts are used for transesterification. These are usually Lewis acids, preferably aluminum tetraisopropylate, titanium tetraisopropylate, silicon tetrachloride or basic catalysts or preparations, e.g. of aluminum oxide with potassium fluoride. The oligomeric silicic acid esters formed in this way then have at least partially bound 1-aza-3,7-dioxabicyclo [3,3,0]octane compounds of the general formula (II) and/or monocyclic oxazolidines of general structure (III). However, the resulting esters usually still contain residues of low alcohols. If small amounts of water or other hydrogen-azide compounds are present during the synthesis of the silicic acid esters, then there is also an exchange of alcohol residues for OH groups. Accordingly, the inventive silicic acid esters usually also contain hydrogen to some extent as a residue ($R^1$, $R^2$, $R^3$, $R^4$ and/or R). Oligosilicic acid esters of low alcohols are commercially available, whereby methanol, ethanol, n-propanol, isopropanol, n-butanol, isobutanol and tert-butanol are usually used for esterification.

Synthesis of oligosilicic acid esters that have undergone transesterification with 1-aza-3,7-dioxabicyclo[3,3,0]octane compounds or monocyclic oxazolidines leads to silicic acid esters, in which some of the residues $R^1$, $R^2$, $R^3$, $R^4$ and R (in formulas I, VII, VIII, IX) are selected from the group consisting of methyl, ethyl, n-propyl, isopropyl, n-butyl, isobutyl and tert-butyl. However, some others of the residues $R^1$, $R^2$, $R^3$, $R^4$ and R (in formulas I, VII, VIII, IX) of the incompletely transesterified oligosilicic acid ester are preferably in the 1-aza-3,7-dioxabicyclo[3,3,0]octane compounds according to general formula (II) and/or monocyclic oxazolidines of general formula (III), in which the structural elements —$CR^5R^6$ and/or —$CR^7R^8$ in compounds of general formula $R^5$—C(=O)—$R^6$ and/or $R^7$—C(=O)—$R^8$ can hydrolyze and thereby release the fragrances. Compounds in which at least 50% of the residues $R^1$, $R^2$, $R^3$, $R^4$ and R of the inventive silicic acid esters are bicyclic oxazolidines (1-aza-3,7-dioxabicyclo[3,3,0]octane compounds according to formula (II)) or monocyclic oxazolidines (according to formula (III)) are preferred. The completely transesterified oligosilicic acid esters are especially preferred within the scope of the present invention. These are compounds in which each residue $R^1$, $R^2$, $R^3$, $R^4$ and R (in formulas I, VII, VIII, IX) is a 1-aza-3,7-dioxabicyclo[3,3,0]octane compound according to general formula (II) and/or a monocyclic oxazolidine according to general formula (III).

The degrees of oligomerization "m" and "n" of the inventive silicic acid esters are between 2 and 20. In preferred compounds, m and/or n assume values between 2 and 15, preferably between 2 and 12 and in particular between 3 and 10, with special preference for the values 4, 5, 6, 7 and 8. If n in formula (1), for example, has the value 2, then the resulting compound has two —$OR^2$ units and two —$OR^4$ units. According to the invention, an $R^2$ residue (in the first —$OR^2$) may then be, for example, a 1-aza-3,7-dioxa-bicyclo[3,3,0] octane compound or a monocyclic oxazolidine, and the other $R^2$ residue (in the second —$OR^2$) may be a hydrogen, an alkyl residue with 1 to 20 carbon atoms or a perfume alcohol residue. However, the $R^2$ residue in the second —$OR^2$ may also be a 1-aza-3,7-dioxabicyclo[3,3,0]octane compound or a monocyclic oxazolidine.

The two $R^4$ residues (in —$OR^4$) are also independent of one another and may preferably be the same or different.

Since the starting compounds for the synthesis of the inventive compounds are preferably not pure substances for economic reasons but instead are technical-grade mixtures of oligosilicic acid esters of low alcohols with different degrees of oligomerization, then a distribution of degrees of oligomerization also occurs in the inventive esters, which may correspond to that in the starting material or may be modified by the reaction conditions.

The compounds of general formula (II) are synthesized, for example, by reacting amino alcohols, preferably 2-amino-1, 3-propanediol derivatives with aldehydes, ketones or mixtures of ketones and aldehydes, which can preferably be described by the general formulas $R^5$—C(=O)—$R^6$ and $R^7$—C(=O)—$R^8$ with ring closure. The reaction is preferably performed in a suitable solvent or in situ. Suitable solvents include, for example, aromatic hydrocarbons such as toluene. The reaction is preferably performed at a temperature in the range of 80° C. to 150° C., especially preferably 100° C. to 140° C. For example, the amino alcohol is placed in the solvent together with the desired ketone or aldehyde under a nitrogen atmosphere. Then the reaction mixture is heated, whereupon the solids gradually go into solution. It is then often heated at reflux on a water separator. The resulting reaction product is isolated by conventional methods and optionally purified. It has been found here that in the reaction of substoichiometric amounts of aldehydes and/or ketones, monocyclic compounds are also present in the product mixture. The amount of bicyclic (oxazolidine) compounds to monocyclic (oxazolidine) compounds can be adjusted easily through the choice of the molar ratio between aldehyde/ketone and 2-amino-1,3-propanediol. Mixtures containing either a large amount of bicyclic or monocyclic oxazolidines are especially preferred.

Such mixtures preferably contain at least 50 wt %, preferably at least 65 wt %, in particular at least 80 wt % bicyclic structures of monocyclic oxazolidines, depending on how the molar ratio between aldehyde/ketone and 2-amino-1,3-propanediol has been adjusted.

If there is a mixture with a large amount of bicyclic oxazolidines, for example, then the resulting reaction product before transesterification preferably has hydrogen as a residue in position $R^{10}$ (formula (II)) or an alkyl residue, which may be substituted by one or two hydroxyl groups and/or an amino group and/or in which up to 8 nonvicinal —$CH_2$ groups may be replaced by —O—. This reaction product is then transesterified with oligosilicic acid esters of low alcohols, as already described above, to yield the inventive silicic acid esters.

The mixture is preferably used here without separating the monocyclic (oxazolidine) compounds in the product mixture from the bicyclic (oxazolidine compounds).

The inventive silicic acid esters are characterized by good hydrolysis stability and can also be used in aqueous media and/or in production processes for granules without suffering excessive losses of activity. The inventive silicic acid esters are preferably used as pro-fragrances, in particular to prolong the fragrance effect of fragrances. In this way, liquid detergents and cleaning agents such as liquid detergents, fabric softeners, hand dishwashing agents, cleaning agents for hard surfaces, floor polish, etc. are just as conceivable as solid detergents and cleaning agents, e.g. textile detergent granules, machine dishwashing agents or cleaning and abrasive agents. Likewise, the inventive silicic agent esters may be used in cosmetic agents for treatment of skin and hair. Here again, liquid agents such as shower soaps, deodorants and shampoos as well as solid agents such as pieces of soaps are both intended.

The inventive compounds of general formulas (I), (VII), (VIII) and (IX) are used as pro-fragrances according to the invention. The term "pro-fragrance" describes derivatives of fragrance aldehydes and fragrance ketones or perfume alcohols, which release the original fragrance aldehydes and fragrance ketones or perfume alcohols under ambient conditions. Ambient conditions here are the typical ambient conditions in the living space of a human and/or the conditions encountered on human skin. Under ambient conditions, the compounds of general formulas (I), (VII), (VIII) and (IX) break down slowly in the reversal of the production process, releasing the original fragrance aldehydes and fragrance ketones and/or perfume alcohols. The chemically bound fragrance aldehydes and fragrance ketones or perfume alcohols are cleaved at the bond site, thereby releasing the perfumes again.

Another subject matter of the present invention is therefore detergents or cleaning agents containing the inventive silicic acid esters.

In an especially preferred embodiment, the detergent and cleaning agent is a fabric softener.

The inventive silicic acid esters can be introduced in varying amounts depending on the type and intended purpose of the agents to be perfumed. Detergents or cleaning agents usually contain the inventive pro-fragrances in amounts of 0.001 to 10 wt %, preferably 0.01 to 5 wt %, especially preferably 0.02 to 3 wt %, and in particular in amounts of 0.05 to 2 wt %, each based on the total composition of the agent in question. The total amount of the fragrances in the inventive detergents or cleaning agents, however, amounts to preferably between 0.01 and 5 wt %, especially preferably between 0.1 and 3 wt % and most especially preferably between 0.5 and 2 wt %, based on the total amount of the agent. Mixtures of different fragrances (from the various fragrance classes mentioned above) which jointly create an appealing fragrance note are preferred. In this case, the total amount of the at least one fragrance is the amount of all fragrances in the mixture together, based on the total amount of the agent.

Detergents or cleaning agents preferably contain the inventive silicic acid esters in amounts of 0.001 to 10 wt %, preferably from 0.01 to 5 wt %, especially preferably from 0.02 to 3 wt % and in particular in amounts of 0.05 to 2 wt %, each based on the total composition of the detergent and cleaning agent are preferred.

In another preferred embodiment, the inventive agents are powdered or granular agents. The particulate components can be produced by spray drying, simple mixing or complex granulation methods, e.g. fluidized-bed granulation.

In another preferred embodiment, the detergents or cleaning agents are in the form of molded bodies, which are produced by a press agglomeration process, i.e. tableting, which is divided into four sections: dosing, compressing (elastic deformation), plastic deformation and ejection. Accordingly, the detergents or cleaning agents are preferably in the form of molded bodies, whereby these are preferably tablets which may consist of a single phase or multiple different phases, in particular two or three phases.

Production is performed by first dry mixing the ingredients, which may be entirely or partially pregranulated, and then placing them in a mold, in particular pressing to form tablets, whereby it is possible to rely on traditional methods.

The premix is preferably compressed in a so-called die between two rams to form a solid compressed article.

To facilitate the disintegration of highly compressed molded articles, it is possible to incorporate disintegration aids, so-called tablet disintegrants, to shorten the disintegration times.

The detergents and cleaning agents may of course contain additional conventional ingredients of detergents and cleaning agents. The usual ingredients are preferably selected from the group of surfactants, fragrances, builder substances and bleaching agents, enzymes and other active substances. The essential ingredients of detergents and cleaning agents include surfactants in particular.

Depending on the intended purpose of the inventive agents, the surfactant content will be selected to be higher or lower. The surfactant content of detergents is usually between 10 and 40 wt %, preferably between 12.5 and 30 wt % and in particular between 15 and 25 wt %, whereas cleaning agents for machine dishwashing, for example, contain between 0.1 and 10 wt %, preferably between 0.5 and 7.5 wt % and in particular between 1 and 5 wt % surfactants.

These surface-active substances come from the group of anionic, nonionic, zwitterionic or cationic surfactants, but anionic surfactants are definitely preferred for economic reasons and because of their performance spectrum in washing and cleaning.

Suitable anionic surfactants include in principle all anionic surface-active substances suitable for use on the human body. These are characterized by a water-solubilizing anionic group, e.g. a carboxylate, sulfate, sulfonate or phosphate group and a lipophilic alkyl group having approximately 8 to 30 carbon atoms. In addition, glycol or polyglycol ether groups, ester groups, ether groups and amide groups as well as hydroxyl groups may also be present in the molecule. Examples of suitable anionic surfactants in the form of the sodium, potassium and ammonium salts as well as the mono-, di- and trialkanolammonium salts with 2 to 4 carbon atoms in the alkanol group include:

linear and branched fatty acids with 8 to 30 carbon atoms (soaps),
ether carboxylic acids of the formula $R^{14}$—O—($CH_2$—$CH_2$O)x-$CH_2$—COOH, in which $R^{14}$ is an alkyl group with 8 to 30 carbon atoms and x=0 or 1 to 16,
acyl sarcosides with 8 to 24 carbon atoms in the acyl group,
acyl taurides with 8 to 24 carbon atoms in the acyl group,
acyl isethionates with 8 to 24 carbon atoms in the acyl group,
sulfosuccinic acid mono- and dialkyl esters with 8 to 24 carbon atoms in the alkyl group and sulfosuccinic acid monoalkylpolyoxyethylene esters with 8 to 24 carbon atoms in the alkyl group and 1 to 6 oxyethyl groups,
linear alkylsulfonates with 8 to 24 carbon atoms,
linear alpha-olefinsulfonates with 8 to 24 carbon atoms,
alpha-sulfo fatty acid methyl esters of fatty acids with 8 to 30 carbon atoms,
alkyl sulfates and alkylpolyglycol ether sulfates of the formula $R^{15}$—O($CH_2$—$CH_2$O)$_x$—$OSO_3H$, in which $R^{15}$ is preferably a linear alkyl group with 8 to 30 carbon atoms and x=0 or 1 to 12,
mixtures of surface-active hydroxysulfonates,
sulfated hydroxyalkyl polyethylene and/or hydroxyalkylene propylene glycol ethers,
sulfonates of unsaturated fatty acids with 8 to 24 carbon atoms and 1 to 6 double bonds,
esters of tartaric acid and citric acid with alcohols which are the addition products of approximately 2-15 molecules of ethylene oxide and/or propylene oxide onto fatty alcohols with 8 to 22 carbon atoms,
alkyl and/or alkenyl ether phosphates of the formula (E1-I),

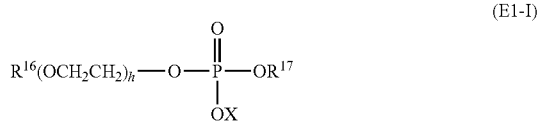

in which $R^{16}$ preferably stands for an aliphatic hydrocarbon residue with 8 to 30 carbon atoms, $R^{17}$ stands for hydrogen, a $(CH_2CH_2O)_n R^{18}$ residue or X, h stands for numbers from 1 to 10 and X stands for hydrogen, an alkali or alkaline earth metal or $NR^{19}R^{20}R^{21}R^{22}$, where $R^{19}$ to $R^{21}$ independently of one another stand for hydrogen or a $C_1$ to $C_4$ hydrocarbon residue,
sulfated fatty acid alkylene glycol esters of formula (E1-II)

in which $R^{22}CO$— stands for a linear or branched aliphatic saturated or unsaturated acyl residue with 6 to 22 carbon atoms, alk stands for $CH_2CH_2$, $CHCH_3CH_2$ and/or $CH_2CHCH_3$, h stands for numbers from 0.5 to 5, and M stands for a cation,
monoglyceride sulfates and monoglyceride ether sulfates of the formula (E1-III)

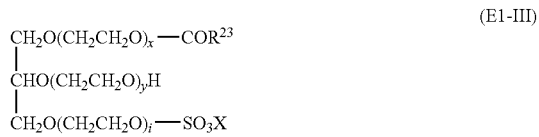

in which $R^{23}CO$ stands for a linear or branched acyl residue with 6 to 22 carbon atoms, x, y and i in total stand for 0 or for numbers from 1 to 30, preferably 2 to 10, and X stands for an alkali or alkaline earth metal. Typical examples of monoglyceride (ether) sulfates suitable in the sense of this invention include the reaction products of lauric acid monoglyceride, coconut fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Monoglyceride sulfates of the formula (E1-III), in which $R^{23}CO$ stands for a linear acyl residue with 8 to 18 carbon atoms, are preferred,
amide ether carboxylic acids,
condensation products of $C_8$-$C_{30}$— fatty alcohols with protein hydrolysates and/or amino acids and their derivatives with which those skilled in the art are familiar as protein fatty acid condensates, e.g. the Lamepon® products, Gluadin® products, Hostapon® KCG or the Amisoft® products.
Preferred anionic surfactants are alkyl sulfates, alkylpolyglycol ether sulfates and ether carboxylic acids with 10 to 18 carbon atoms in the alkyl group and up to 12 glycol ether groups in the molecule, sulfosuccinic acid mono- and dialkyl esters with 8 to 18 carbon atoms in the alkyl group and sulfosuccinic acid mono-alkyl polyoxyethyl esters with 8 to 18 carbon atoms in the alkyl group and 1 to 6 oxyethyl groups, monoglyceride sulfates, alkyl and alkenyl ether phosphates as well as protein fatty acid condensate.

Cationic surfactants may likewise be used. Preferred according to the present invention are cationic surfactants of the type of quaternary ammonium compounds, ester quats and amidoamines. The cationic surfactants in the inventive agents are preferably present in amounts of 0.05 to 10 wt %, based on the total use preparation. Amounts of 0.1 to 5 wt % are especially preferred.

In addition or instead of the cationic surfactants, the agents may contain other surfactants or emulsifiers, whereby both anionic and ampholytic and nonionic surfactants and all types of known emulsifiers are suitable in principle. The group of ampholytic or amphoteric surfactants includes zwitterionic surfactants and ampholytes. The surfactants may already have an emulsifying effect.

Zwitterionic surfactants are surface-active compounds which have at least one quaternary ammonium group and at least one —$COO^{(-)}$— or —$SO_3^{(-)}$ group in the molecule. Ampholytes are understood to be surface-active compounds which have at least one free amino group and at least one —COOH— or —$SO_3H$ group in the molecule in addition to a $C_8$-$C_{24}$ alkyl group or acyl group and are capable of forming internal salts. Nonionic surfactants contain as the hydrophilic group, e.g. a polyol group, a polyalkylene glycol ether group or a combination of polyol and polyglycol ether groups.

Nonionic surfactants contain as the hydrophilic group, e.g. a polyol group, a polyalkylene glycol ether group or a combination of polyol and polyglycol ether groups. Preferred nonionic surfactants have proven to be the alkylene oxide addition products onto saturated linear fatty alcohols and fatty acids each with 2 to 30 mol ethylene oxide per mol fatty alcohol and/or fatty acid. Preparations with excellent properties are also obtained when they contain fatty acid esters of ethoxylated glycerol as the nonionic surfactants.

These compounds are characterized by the following parameters. The alkyl residue contains 6 to 22 carbon atoms and may be both linear and branched. Primary linear aliphatic residues and those with methyl branching in position 2 are preferred. Such alkyl residues include, for example, 1-octyl, 1-decyl, 1-lauryl, 1-myristyl, 1-cetyl and 1-stearyl. Especially preferred are 1-octyl, 1-decyl, 1-lauryl, 1-myristyl. When using so-called "oxo alcohols" as starting materials, compounds with an odd number of carbon atoms in the alkyl chain are predominant as the starting materials.

In addition, the sugar surfactants may also be present as nonionic surfactants. These are preferably present in amounts of 0.1 to 20 wt %, based on the respective total composition. Amounts of 0.5 to 15 wt % are especially preferred, and amounts of 0.5 to 7.5 wt % are most especially preferred.

The additional surfactants are usually used in amounts of 0.1 to 45 wt %, preferably 0.5 to 30 wt % and most especially preferably from 0.5 to 25 wt %, based on the respective total composition. The amount used depends to a significant extent on the purpose to be fulfilled by the inventive agent. If it is a shampoo or another cleaning agent, a surfactant content greater than 45 wt % is customary.

These agents may also contain at least one emulsifier. Emulsifiers act at the phase interface to form water-stable and/or oil-stable adsorption layers which protect the disperse droplets from coalescing and thereby stabilize the emulsion. Therefore, emulsifiers are constructed from a hydrophobic part of a molecule and a hydrophilic part. Hydrophilic emulsifiers preferentially form O/W emulsions and hydrophobic emulsifiers preferentially form W/O emulsions. The choice of these emulsifying surfactants or emulsifiers will depend on the substances to be dispersed and the respective external phase as well as the finely divided aspect of the emulsion. The emulsifiers are preferably used in amounts of 0.1 to 25 wt %, in particular 0.1 to 3 wt %, based on the respective total composition.

Another important group of detergent and cleaning agent ingredients are the builder substances. This class of substance is understood to include both organic and inorganic builder substances. These are compounds which may perform a carrier function in the inventive agents as well as acting as water-softening substances in application. The agents preferably contain builders in amounts of 0 to 20 wt %, preferably 0.01 to 12 wt %, in particular 0.1 to 8 wt %, most extremely preferably 0.3 to 5 wt %, based on the composition.

In addition to the aforementioned ingredients, the inventive detergents and cleaning agents may additionally contain one or more substances from the group of bleaching agents, bleach activators, enzymes, pH-adjusting agents, fluorescent agents, dyes, foam inhibitors, silicone oils, antiredeposition agents, optical brighteners, graying inhibitors, dye transfer inhibitors, corrosion inhibitors and silver protectants.

Detergents and cleaning agents according to the present invention may also be dishwashing agents. The inventive dishwashing agents may contain corrosion inhibitors to protect the machine or the items washed, where silver protectants are especially important in the area of machine dishwashing.

Essentially the agents may have different physical states. In another preferred embodiment, the detergents or cleaning agents are liquid or gel agents, in particular liquid detergents or liquid dishwashing agents or cleaning gels, whereby they may also be gel-cleaning agents for rinsing toilets in particular.

Additional typical cleaning agents which may contain the inventive silicic acid esters are liquid or gelatinous cleaners for hard surfaces, in particular so-called all-purpose cleaners, glass cleaners, floor and bathroom cleaners and special embodiments of such cleaners, including acidic or alkaline forms of all-purpose cleaners as well as glass cleaners with a so-called spot-free effect. These liquid cleaning agents may be present in one phase or in multiple phases. In an especially preferred embodiment, the cleaners have two different phases. Cleaner here is in the broadest sense a term for formulations, usually containing surfactant, with a very broad area of use and a great variation in composition depending on that.

In a preferred variant, the detergents and cleaning agents, in particular in the form of molded articles such as tablets contain 0.5 to 10 wt %, preferably 3 to 7 wt % and in particular 4 to 6 wt % of one or more disintegrants, each based on the weight of the molded article.

Another subject matter of the present invention is cosmetic agents and/or agents for treatment of hair or skin containing the inventive silicic acid esters.

These cosmetic agents preferably contain the inventive silicic acid esters in amounts of 0.001 to 10 wt %, preferably 0.01 to 5 wt %, especially preferably 0.02 to 3 wt % and in particular in amounts of 0.05 to 2 wt %, each based on the total composition of the cosmetic agent. The total amount of the fragrances in the cosmetic agents is, however, preferably between 0.01 and 5 wt %, especially preferably between 0.01 and 3 wt % and most especially preferably between 0.5 and 2 wt %, based on the total amount of the agent. Mixtures of different fragrances (from the various aforementioned fragrance classes), which together produce an attractive fragrance note, are preferred. In this case, the total amount of the at least one fragrance is the amount of all fragrances in the mixture together, based on the total amount of the agent.

In a preferred embodiment, the cosmetic agents are aqueous preparations containing surface-active ingredients, which are suitable in particular for treatment of keratin fibers, in particular human hair or for treatment of skin. Additional cosmetic agents preferred according to the invention are agents for influencing body odor. Deodorizing agents are intended here in particular.

Another subject matter of the present invention is the use of the inventive silicic acid esters for prolonging the fragrance effect of fragrances. Because of the excellent suitability of the inventive compounds for use in detergents and cleaning agents, the use of the inventive silicic acid esters in liquid or solid detergents and cleaning agents, especially preferably as a fragrance, is another subject matter of the present invention. The inventive silicic acid esters are likewise excellently suited for use in cosmetic agents, so another subject matter of the present invention is the use of the inventive silicic acid esters in cosmetic agents for treatment of skin and hair, especially preferably as a fragrance. Silicic acid esters containing fragrance aldehydes or fragrance ketones as the fragrance residues are preferred for use here. The inventive silicic acid esters are preferably used together with other fragrances. The fragrances may preferably be in the form of silicic acid esters or in mixtures with other fragrances which are not pro-fragrances. The inventive silicic acid esters in the aforementioned fields of use are preferably used in amounts of 0.001 to 10 wt %, preferably 0.01 to 5 wt %, especially preferably from 0.02 to 3 wt % and in particular in amounts of 0.05 to 2 wt %, each based on the agent.

Another subject matter of the present invention is the method for prolonging the fragrance perception of detergents or cleaning agents, fabric softeners or cosmetics or solid surfaces treated with these products, characterized in that the inventive silicic acid esters or mixtures thereof are added to the detergents or cleaning agents, fabric softeners or cosmetics. The fragrances which are bound to the inventive silicic acid esters are preferably gradually released by hydrolysis.

The inventive silicic acid esters may be used as the exclusive fragrance but it is also possible to use fragrance mixtures consisting only in part of the inventive silicic acid esters. Such mixtures have the advantage that the ingredients of the fragrance mixture which are not present in the form of silicic acid esters are also improved with regard to the stability of the fragrance impression. Thus, in particular fragrance mixtures containing 1 to 50 wt %, preferably 5 to 40 wt % and in particular max. 30% silicic acid esters may be used. In other embodiments in which the delayed fragrance effect of the carrier-bound form is to be utilized in particular, at least 30 wt %, preferably at least 40 wt % and in particular at least 50 wt % of the total perfume contained in the agent is advantageously introduced into the agents via the inventive silicic acid esters, while the remaining 70 wt %, preferably 60 wt % and in particular 50 wt % of the total perfume contained in the agent is sprayed on in the usual way or otherwise introduced into the agents. The inventive use may also advantageously be characterized in that the silicic acid esters are used together with other fragrances.

While particular embodiments of the present invention have been illustrated and described, it would be obvious to those skilled in the art that various other changes and modifications can be made without departing from the spirit and scope of the invention.

Other than where otherwise indicated, or where required to distinguish over the prior art, all numbers expressing quantities of ingredients herein are to be understood as modified in all instances by the term "about". As used herein, the words "may" and "may be" are to be interpreted in an open-ended, non-restrictive manner. At minimum, "may" and "may be" are to be interpreted as definitively including, but not limited to, the composition, structure, or act recited.

As used herein, and in particular as used herein to define the elements of the claims that follow, the articles "a" and "an" are synonymous and used interchangeably with "at least one" or "one or more," disclosing or encompassing both the singular and the plural, unless specifically defined herein otherwise. The conjunction "or" is used herein in both in the conjunctive and disjunctive sense, such that phrases or terms conjoined by "or" disclose or encompass each phrase or term alone as well as any combination so conjoined, unless specifically defined herein otherwise.

The description of a group or class of materials as suitable or preferred for a given purpose in connection with the invention implies that mixtures of any two or more of the members of the group or class are equally suitable or preferred. Description of constituents in chemical terms refers unless otherwise indicated, to the constituents at the time of addition to any combination specified in the description, and does not necessarily preclude chemical interactions among the constituents of a mixture once mixed. Steps in any method disclosed or claimed need not be performed in the order recited, except as otherwise specifically disclosed or claimed.

Changes in form and substitution of equivalents are contemplated as circumstances may suggest or render expedient. Although specific terms have been employed herein, such terms are intended in a descriptive sense and not for purposes of limitation.

The following Examples further illustrate the preferred embodiments within the scope of the present invention, but are not intended to be limiting thereof. It is understood that the examples and embodiments described herein are for illustrative purposes only and that various modifications or changes in light thereof will be suggested to one skilled in the art without departing from the scope of the present invention. The appended claims therefore are intended to cover all such changes and modifications that are within the scope of this invention.

EXAMPLES

Synthesis of 1-aza-3,7-dioxa-bicyclo[3,3,0]octane and/or 1,3-oxazolidine derivatives

AA1

General operating procedure for synthesis of 1-aza-3,7-dioxabicyclo[3,3,0]octane and/or 1,3-oxazolidine derivatives, ratio of amino alcoholic/fragrance aldehyde and/or fragrance ketone First the amino alcohol is put under a nitrogen atmosphere and added with the aldehyde and/or ketone in a 1:2 ratio (1-aza-3,7-dioxa-bicyclo[3,3,0]octane derivatives) and/or 1:1 ratio (1,3-oxazolidine derivatives) in toluene. The reaction mixture is heated to T=120° C., while the amino alcohol slowly dissolves. Refluxing on the water separator for seven hours. Treatment by rotary evaporator and drying of the clear slightly yellowish solution in a high vacuum.

AA2

General operating procedure for synthesis of 1-aza-3,7-dioxabicyclo[3,3,0]octane and/or 1,3-oxazolidine derivatives, ratio of amino alcohol/fragrance aldehyde and/or ketone in situ The amino alcohol is first put under a nitrogen atmosphere and added with the aldehyde and/or ketone in a 1:2 ratio (1-aza-3,7-dioxa-bicyclo[3,3,0]octane derivatives) and/or 1:1 ratio (1,3-oxazolidine derivatives) in toluene. The reaction mixture is heated to T=100° C. to 140° C., the reactants slowly dissolving or melting. The reaction mixture is heated until no more reaction water can be distilled off. The clear, slightly yellowish solution is dried in a high vacuum. Further purification of the corresponding 1-aza-3,7-dioxa-bicyclo[3,3,0]-octane and/or 1,3-oxazolidine derivatives may be performed by column chromatography with silica gel as the stationary phase. For example, phenyl-1-methyleneheptyl-1, 3-oxazolidin-4-yl-methanol is successfully purified at room temperature with silica gel as the stationary phase and with a toluene/ethyl acetate mixture 15:1 as eluents. The Rf value of the substance identified above is 0.09.

2. Synthesis of the Inventive Silicic Acid Esters 2.1. AA3

Transesterification of AA1 or AA2 to the Silicic Acid Esters

The inventive silicic acid esters are synthesized according to the present invention by simple transesterification of oligosilicic acid esters of low alcohols with the compounds obtained from AA1 or AA2. Depending on the reaction time and reaction conditions, the low alcohols are split off and the compounds from AA1 and/or AA2 are bonded, and the alcohols along Si—O—Si chains or rings are more easily exchanged than are the terminal alcohols. Such transesterifications may be performed, e.g. as described in the publication by H. Steinmann, G. Tschernko, H. Hamann, Z. *Chem.* 3, 1977, pp. 89-92. The content of this publication is explicitly regarded as the disclosure content of the present patent application for the synthesis of silicic acid esters. The commercial silicic acid esters are usually used as the educts. In particular the ethanol ester which can be obtained from Wacker, Burghausen, for example, should be mentioned here. The transesterification can be controlled exclusively through an increase in temperature and by distilling off the low-boiling by-products. However, it is preferable if catalysts are used for transesterification. These are usually Lewis acids, preferably aluminum triisopropylate, titanium tetraisopropylate, silicon tetrachloride or basic catalysts or preparations such as aluminum oxide with potassium fluoride.

2.2. AA4

Polymer-Like Reaction to Silicic Acid Ester

The amino alcohol may also be reacted directly with partially hydrolyzed tetraethoxy silane while passing nitrogen through the mixture at 120° C., whereupon ethanol is split off. Next the mixture is cooled and the aldehyde and/or the ketone is/are added and heated again to 110° C. The reaction water is distilled off in a high vacuum at 110° C. After a reaction time of approximately 4 hours, the reaction product is cooled to room temperature, yielding a clear, highly viscous liquid. The reaction step of synthesis of the inventive silicic acid esters according to AA3 or AA4 can easily take place by GC analysis. At regular intervals, a sample is taken from the reaction solution and used to determine the amount of remaining 1-aza-3,7-dioxa-bicyclo[3,3,0]octane and/or 1,3-oxazolidine derivatives by GC analysis. For example, the reaction of 1-aza-3,7-dioxa-2,8-diheptyl-5-methyloxy-bicyclo[3,3,0] octane can be tracked with the following GC analysis:

| | |
|---|---|
| GC device: | Hewlett Packard 5890 series II |
| Column: | HP 1 crosslinked methylsilicone gum (25 m × 0.32 mm × 0.17 μm) |
| Starting temperature: | 45° C. |
| Heating rate: | 15° C./min |
| Final temperature: | 300° C. |
| Final time: | 5 min |
| Retention time of 1-aza-3,7-dioxa-2,8-diheptyl-5-methyloxybicyclo[3,3,0]octane | approximately 13.8 min |

After the reaction according to AA3 or AA4, the peak for the free 1-aza-3,7-dioxa-2,8-diheptyl-5-methyloxy-bicyclo[3,3,0]octane at approximately 13.8 min has disappeared.

Smell Test

A commercial perfume-free detergent was mixed first with 0.5 wt % of the inventive silicic acid ester and next with 0.4 wt % of the free fragrance. The laundry was washed at 60° C. with 150 g of this powder and re-rinsed three times with clear water. After spin-drying, the fragrance of the wet laundry was evaluated, then the laundry was line-dried. The fragrance of the dry laundry was evaluated immediately, after one day and after seven days with the laundry being stored in plastic bags.

The laundry pairs were evaluated by seven experts (perfumers) in direct comparison with regard to the fragrance intensity. The results of these tests are shown in Table 1.

| | Definition of the scaling: |
|---|---|
| 5 | can be smelled very well |
| 4 | can be smelled well |
| 3 | can be smelled somewhat |
| 2 | little fragrance perceptible |
| 1 | no fragrance/hardly any fragrance perceptible |

TABLE 1

Results of the smell test on laundry in Vernel fabric softener 4 times

| Product | Wet laundry | Day 1 | Day 7 |
|---|---|---|---|
| Pure fragrance (octanal) | 5 | 5 | 3.2 | 2.8 |
| Inventive pro-fragrance* | 2.5 | 3 | 4.8 | 3.6 |

*1-aza-3,7-dioxa-2,8-diheptyl-5-hydroxymethyl-bicyclo[3,3,0]octane silicic acid ester

What is claimed:

1. A silicic acid ester of the general formula (I)

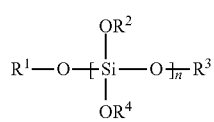

(I)

wherein at least one of the residues $R^1$, $R^2$, $R^3$ and $R^4$ independently of one another is a 1-aza-3,7-dioxabicyclo[3,3,0]octane compound of the general formula (II),

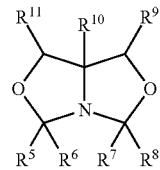

(II)

where $R^5$, $R^6$, $R^7$, and $R^8$ independently of one another are hydrogen or residues that yield one or more of a fragrance aldehyde or a fragrance ketone of the general formulae $R^5$—C(=O)—$R^6$ or $R^7$—C(=O)—$R^8$ upon hydrolysis, wherein at least one of $R^5$—C(=O)—$R^6$ or $R^7$—C(=O)—$R^8$ comprises a fragrance aldehyde selected from the group consisting of citral, melonal, lilial, floralozone, canthoxal, 3-(4-ethylphenyl)-2,2-dimethylpropanal, 3-(4-methoxyphenyl)-2-methyl-propanal, 4-(4-hydroxy-4-methylpentyl)-3-cyclohexene-1-carboxaldehyde, phenyl-acetaldehyde, methyl nonyl acetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropyl-phenyl)-2-methyl-propan-1-al, 3-(4-ethylphenyl)-2,2-dimethylpropan-1-al, 3-(4-tert-butylphenyl)-2-methyl-propanal, 3-(3,4-methylenedioxyphenyl)-2-methylpropan-1-al, 3-(4-ethylphenyl)-2,2-dimethylpropanal, 3-(3-isopropylphenyl)butan-1-al, 2,6-dimethylhept-5-en-1-al, n-decanal, n-undecanal, n-dodecanal, 3,7-dimethyl-2,6-octadien-1-al, 4-methoxybenzaldehydes, 3-methoxy-4-hydroxybenzaldehydes, 3-ethoxy-4-hydroxybenzaldehydes, 3,4-methylenedioxybenzaldehyde and 3,4-dimethoxybenzaldehyde, adoxal, anisaldehyde, cumal, ethylvanillin, florhydral, helional, heliotropin, hydroxycitronellal, koavone, lauryl aldehyde, lyral, methyl-nonylacetaldehyde, bucinal, phenylacetaldehyde, undecylenealdehyde, vanillin, 2,6,10-trimethyl-9-undecenal, 3-dodecen-1-al, alpha-n-amylcinnamaldehyde, 4-methoxy-benzaldehyde, 3-(4-tert-butylphenyl)-propanal, 2-methyl-3-paramethoxyphenylpropanal, 2-methyl-4-(2,6,6-trimethyl-2(1)-cyclohexen-1-yl)but-anal, 3-phenyl-2-propenal, cis-/trans-3,7-dimethyl-2,6-octadien-1-al, 3,7-dimethyl-6-octen-1-al, [(3,7-dimethyl-6-octenyl)oxy]acetaldehyde, 4-isopropyl-benz-aldehyde, 1,2,3,4,5,6,7,8-octahydro-8,8-dimethyl-2-naphthaldehyde, 2,4-dimethyl-3-cyclohexene-1-carboxaldehyde, 1-decanal, decylaldehyde, 2,6-dimethyl-5-heptenal, 4-(tricyclo[5.2.1.0(2,6)]-decylidene-8)-butanal, octahydro-4,7-methano-1-indenecarboxaldehyde, 3-ethoxy-4-hydroxybenzaldehyde, para-ethyl-alpha,alpha-dimethylhydrocinnamaldehyde, alpha-methyl-3,4-(methylenedioxy)-hydrocinnamaldehyde, 3,4-methylenedioxybenzaldehyde, alpha-n-hexylcinnamaldehyde, m-cumene-7-carboxaldehyde, alpha-methylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-do-decanal, 2,4-dimethyl-cyclohexene-3-carboxaldehyde, 4-(4-hydroxy-4-methyl-pentyl)-3-cylohexene-1-carboxaldehyde, 7-methoxy-3,7-dimethyloctan-1-al, 2-methylundecanal, 2-methyldecanal, 1-nonanal, 1-octanal, 2,6,10-trimethyl-5,9-undecadienal, 2-methyl-3-(4-tert-butyl)propanal, dihydrocinnamaldehyde, 1-methyl-4-(4-methyl-3-pentenyl)-3-cyclohexene-1-carboxaldehyde, 5- or 6-meth-oxyhexahydro-4,7-methanoindane-1- or 2-carboxaldehyde, 3,7-dimethyl-octan-1-al, 1-undecanal, 10-undecen-1-al, 4-hydroxy-3-methoxybenzaldehyde, 1-methyl-3-(4-methylpentyl)-3-cyclohexene-carboxalde-hyde, 7-hydroxy-3,7-di-methyloctanal, trans-4-decenal, 2,6-nonadienal, para-tolylacetaldehyde, 4-methylphenyl-acetaldehyde, 2-methyl-4-(2,6,6-trimethyl-1-cyclo-hexen-1-yl)-2-butenal, ortho-methoxycinnamaldehyde 3,5,6-trimethyl-3-cyclohexenecarboxaldehyde, 3,7-dimethyl-2-methylene-6-octenal, phenoxy-acetalde-hyde, 5,9-dimethyl-4,8-decadienal, peonyaldehyde (6,10-dimethyl-3-oxa-5,9-undecadien-1-al), hexa-hydro-4,7-methanoindane-1-carboxaldehyde, 2-methyl-octanal, alpha-methyl-4-(1-methylethyl)benzolacetal-dehyde, 6,6-dimethyl-2-norpinene-2-propionaldehyde, para-methylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo-[2.2.1]-hept-5-ene-2-carbaldehyde, 9-decenal, 3-methyl-5-phenyl-1-pentanal and methyl nonyl acetaldehyde, and mixtures thereof or a fragrance ketone selected from the group consisting of buccoxime, isojasmone, methyl beta-naphthyl ketone, musk indanone, tonalide, alpha-damascone, beta-damascone, delta-damascone, iso-damascone, damascenone, damarose, methyl dihydro-jasmonate, menthone, carvone, camphor, fenchone, alpha-ionene, beta-ionone, dihydro-beta-ionone, fleura-mone, dihydrojasmone, cis-jasmone, 1-(1,2,3,4,5,6,7,8-octahydro-2,3,8,8-tetramethyl-2-naphthalenyl)-ethan-1-one, methyl cedrenyl ketone, methyl-cedrylone, acetophenone, methylacetophenone, para-methoxy-ac-etophenone, methyl beta-naphthyl ketone, benzylac-etone, para-hydroxyphenyl-butanone, celery ketone, livescone, 6-isopropyldecahydro-2-naphthone, dim-ethyl octenone, 2-sec-butylcyclohexan-1-one, 4-(1-ethoxyvinyl)-3,3,5,5,-tetra-methyl-cyclohexanone, methyl heptenone, 2-(2-(4-methyl-3-cyclohexen-1-yl)-propyl)cyclopentanone, 1-(p-menthen-6(2)-yl)-1-pro-panone, 4-(4-hydroxy-3-methoxyphenyl)-2-butanone, 2-acetyl-3,3-dimethyl-norbornane, 6,7-dihydro-1,1,2,3,3-pentamethyl-4(5H)-indanone, 4-damascol, dulcinyl, cassione, gelsone, hexylone, isocyclemone E, methyl cyclocitrone, methyl lavendel ketone, orivone, para-tert-butyl-cyclohexanone, verdone, delphone, muscone, neobutenone, plicatone, veloutone, 2,4,4,7-tetramethyl-oct-6-en-3-one, tetrameran, hedione, gamma-meth-ylionone, and mixtures thereof, wherein $R^5$, $R^6$, $R^7$, and $R^8$ are not hydrogen at the same time, $R^9$, $R^{11}$ independently of one another are hydrogen, an alkyl residue with 1 to 8 carbon atoms, hydroxyalkyl with 1 to 8 carbon atoms, aminoalkyl, $R^{10}$ is a bond or a divalent alkylene residue with 1 to 8 carbon atoms;

and the remaining residues $R^1$, $R^2$, $R^3$ and $R^4$ independently of one another are selected from hydrogen, an alkyl residue with 1 to 20 carbon atoms, or a perfume alcohol residue, and n assumes values in the range of 2 to 20.

2. A mixture of the silicic acid ester of claim 1 and one or more silicic acid esters of formula (VII),

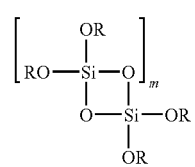

where the residues R independently of one another assume the meanings of the residues $R^1$, $R^2$, $R^3$ or $R^4$ according to formula (I) and m is a number from 2 to 20.

3. A mixture of the silicic acid ester of claim 1 and one or more silicic acid esters of formula (VIII) and/or (IX):

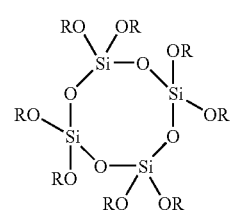

wherein the residues R independently of one another assume the meanings of residues $R^1$, $R^2$, $R^3$ or $R^4$ according to formula (I).

4. The mixture of claim 2, further comprising one or more silicic acid esters of formula (VIII) and/or (IX):

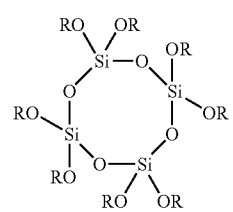

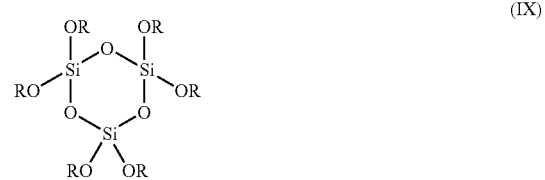

wherein the residues R independently of one another assume the meanings of residues $R^1$, $R^2$, $R^3$ or $R^4$ according to formula (I).

5. The silicic acid ester of claim 1, wherein at least two of the residues $R^1$, $R^2$, $R^3$, $R^4$ comprise a 1-aza-3,7-dioxa-bicyclo[3,3,0]octane compound of general formula (II).

6. The silicic acid ester of claim 1, wherein the bond of the 1-aza-3,7-dioxabicyclo[3,3,0]octane compound of general formula (II) to the silicic acid ester is via the $R^{10}$ residue.

7. The silicic acid ester of claim 1, wherein the residue $R^{10}$ is a divalent alkylene residue.

8. The silicic acid ester of claim 7, wherein the divalent alkylene is methylene or ethylene.

9. A washing or cleaning agent, comprising one or more silicic acid esters of claim 1.

10. A cosmetic agent for treatment of hair or skin, comprising one or more silicic acid esters of claim 1.

* * * * *